United States Patent [19]

Steiner et al.

[11] Patent Number: 4,661,591

[45] Date of Patent: Apr. 28, 1987

[54] PREPARATION OF 4,5-DIHYDRODITHIENO[3,4-B:3',4'-E]AZE-PINE-5,9-DIONE

[75] Inventors: Gerd Steiner, Kirchheim; Marco Thyes, Ludwigshafen, both of Fed. Rep. of Germany

[73] Assignee: BASF Aktiengesellschaft, Fed. Rep. of Germany

[21] Appl. No.: 883,814

[22] Filed: Jul. 9, 1986

[30] Foreign Application Priority Data

Jul. 11, 1985 [DE] Fed. Rep. of Germany ....... 3524743

[51] Int. Cl.$^4$ .................. C07D 495/14; C07D 403/14
[52] U.S. Cl. .................................... 540/495; 540/524; 548/465; 548/527; 546/212

[58] Field of Search ................ 540/495, 524; 548/465, 548/527; 546/212

[56] References Cited

U.S. PATENT DOCUMENTS 4,362,727 12/1982 Steiner et al. ...................... 540/596
4,562,004 12/1985 Steiner .............................. 260/396 R

FOREIGN PATENT DOCUMENTS 0050212 4/1982 European Pat. Off. ............ 540/495

*Primary Examiner*—Robert T. Bond
*Attorney, Agent, or Firm*—Keil and Weinkauf

[57] ABSTRACT

A novel process for the preparation of 4,5-dihydrodithieno[3,4-b:3',4'-e]azepine-5,9-dione is described.

4 Claims, No Drawings

PREPARATION OF 4,5-DIHYDRODITHIENO[3,4-B:3',4'-E]AZEPINE-5,9-DIONE

The present invention relates to a novel process for the preparation of 4,5-dihydrodithieno[3,4-b:3',4'-e]azepine-5,9-dione.

The processes known to date for the preparation of 4,5-dihydrodithieno[3,4-b:3',4'-e]azepine-5,9-dione (cf. German Laid-Open Application No. DOS 3,037,971 in conjunction with German Laid-Open Application No. DOS 3,309,719) are tedious and give very moderate yields, particularly for fairly large batches.

We have found that 4,5-dihydrodithieno[3,4-b:3',4'-e]azepine-5,9-dione of the formula I

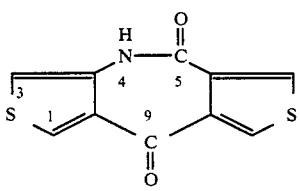

can be prepared very readily by Friedel-Crafts cyclization of thiophene-3,4-dicarboxylic acid 2,5-dichlorothien-3-ylamide of the formula II

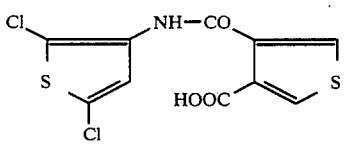

followed by catalytic dechlorination of the resulting 1,3-dichloro-4,5-dihydrodithieno[3,4-b:3',4'-e]azepine-5,9-dione of the formula

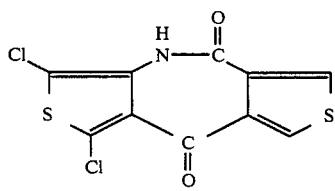

To convert compound II, the latter is first reacted, in the presence of one mole equivalent of a condensing agent, such as a carbodiimide, preferably dicyclohexylcarbodiimide, with a cyclic N-hydroximide, such as N-hydroxysuccinimide, N-hydroxyglutarimide or N-hydroxyphthalimide, to give an activated ester of the formula IV

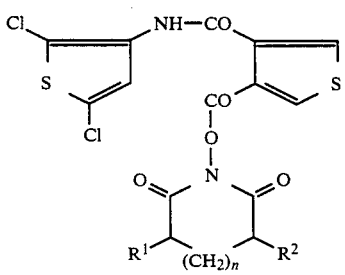

where n is 0, 1 or 2 and $R^1$ and $R^2$ are identical or different and are each $C_1$–$C_4$-alkyl, or, where n is 0, $R^1$ and $R^2$ together with the carbon atoms to which they are bonded form a benzene nucleus. This is advantageously carried out in an inert organic solvent, such as a hydrocarbon, eg. toluene, or in particular a saturated aliphatic or saturated cyclic ether, such as diethyl ether, tetrahydrofuran or dioxane, or in a dipolar aprotic solvent, such as dimethylformamide. As a rule, the reaction is complete in the course of about 1–3 hours at room temperature. The precipitated urea is filtered off under suction or separated off by extraction, and the activated ester IV is isolated by evaporating down the mixture.

The ester IV thus obtained is then subjected to a Friedel-Crafts cyclization reaction. For this purpose, the activated ester IV is converted in the presence of a 5-fold to 12-fold excess of aluminum chloride, in an inert aprotic organic solvent, in particular a saturated aliphatic or saturated cyclic ether, such as diethyl ether, tetrahydrofuran or dioxane, or preferably in a dipolar aprotic solvent, such as dimethylformamide, at from 50° to 120° C. in the course of from 0.5 to 2 hours, to give the 1,3-dichloro-4,5-dihydrodithieno[3,4-b:3',4'-e]azepine-5,9-dione in a smooth reaction.

This reaction sequence must be followed since normal Friedel-Crafts cyclization reactions via the acyl chloride or other activated derivatives do not lead to the 7-membered ring but exclusively to the corresponding imide possessing a 5-membered ring.

1,3-Dichloro-4,5-dihydrodithieno[3,4-b:3',4'-e]-azepine-5,9-dione III in dechlorinated by catalytic hydrogenation using a noble metal catalyst, eg. palladium on carbon, in the presence of an acid acceptor, eg. sodium acetate, sodium carbonate, ammonia or an alkylamine, such as tripropylamine, in an inert organic solvent, in particular a saturated aliphatic or saturated cyclic ether, such as diethyl ether, tetrahydrofuran or dioxane, a dipolar aprotic solvent, preferably dimethylformamide or 1-methyl-pyrrolid-2-one, or a lower alcohol, preferably propanol or isopropanol. Conversion to 4,5-dihydrodithieno-[3,4-b:3',4'-e]azepine-5,9-dione of the formula I is carried out under a hydrogen pressure of from 1 to 3 atmospheres at temperatures from room temperature to 100° C., in the course of from 2 to 8 hours. Where a hydrogen donor, eg. ammonium formate, is used, elemental hydrogen may be dispensed with.

Thiophene-3,4-dicarboxylic acid 2',5'-dichlorothien-3-ylamide of the formula II, which serves as a starting material, is obtained in a simple manner by reacting thiophene-3,4-dicarboxylic anhydride with 2,5-dichloro-3-aminothiophene in an inert organic solvent, such as a hydrocarbon, preferably toluene, a halohydrocarbon or a saturated aliphatic or saturated cyclic ether, such as diethyl ether, tetrahydrofuran or dioxane, at room temperature for from 1 to 5 hours.

In the novel process, 4,5-dihydrodithieno[3,4-b:3',4'-e]azepine-5,9-dione is obtained from readily available starting materials, in very good yield. Moreover, the process can be extrapolated to a large industrial-scale without loss of yield.

The Examples which follow illustrate the invention.

EXAMPLE 1

(a) Thiophene-3,4-dicarboxylic acid 2',5'-dichlorothien-3-ylamide (II)

168.0 g (1 mole) of 2,5-dichloro-3-amino-thiophene in 1.5 l of toluene were added dropwise to 154.4 g (1 mole)

of thiophene-3,4-dicarboxylic anhydride in 2 l of toluene in the course of 45 minutes at room temperature, while stirring thoroughly. Stirring was then continued for 2-3 hours, after which the dense precipitate was filtered off under suction, washed thoroughly with toluene and dried, first in the air and subsequently in a drying oven under reduced pressure. 313 g (97%) of product of melting point 266°-268° C. (decomposition) were obtained.

(b) 1,3-Dichloro-4,5-dihydrodithieno[3,4-b:3',4'-e]azepine-5,9-dione 10.0 g (31.0 millimoles) of N-(2',5'-dichlorothien-3-yl)-2-carboxythiophenecarboxamide were dissolved in 350 ml of tetrahydrofuran, and 3.5 g (31.0 millimoles) of N-hydroxysuccinimide and 6.5 g (31.0 millimoles) of N,N-dicyclohexylcarbodiimide were added to the thoroughly stirred solution. The reaction mixture was stirred for 2 hours at room temperature, after which the precipitated urea was filtered off under suction and washed with a little tetrahydrofuran, and the filtrate was evaporated to dryness. The residue was introduced a little at a time into a melt consisting of 49.2 g (368 millimoles) of $AlCl_3$ and 7.4 ml of dimethylformamide at an internal temperature of 80° C., while stirring thoroughly. The reaction mixture was kept at 90° C. for a further 45 minutes, after which the hot mixture was poured onto ice, acidified with HCl and stirred for some time, and the pale brown solid was then filtered off under suction, washed with $H_2O$ and dried in the air to give 9.1 g (97%) of product which melted at 248°-250° C. after recrystallization from glacial acetic acid.

(c) 4,5-Dihydrodithieno[3,4-b:3',4'-e]azepine-5,9-dione (I)

3.0 g of Pd/C (10%) and 15.0 g (183 millimoles) of finely powedered sodium acetate were added to 19.2 g (63.2 millimoles) of 1,3-dichloro-4,5-dihydrodithieno[3,4-b:3',4'-e]azepine-5,9-dione in 600 ml of 1-methylpyrrolid-2-one, and hydrogenation was carried out in a 2.5 l Rollhofer apparatus for 5 hours under a hydrogen pressure of 200 bar and at 80° C. Thereafter, the mixture was filtered under suction, the residue was washed with pyrrolidone and then $H_2O$, the filtrate was poured onto 5 l of ice water, acidified with concentrated HCl and stirred for a further hour, after which the solid was filtered off under suction with thorough washing with $H_2O$, and the crude product was dried. The yield was 12.6 g (85%) and the melting point 267°-270° C.

EXAMPLE 2

(a) Thiophene-3,4-dicarboxylic acid mono-[N-(2,5-dichlorothien-3-yl)]-amide (II)

202.4 g (2.00 moles) of triethylamine were added dropwise to 308.8 g (2.00 moles) of thiophene-3,4-dicarboxylic anhydride and 416.8 g (2.04 moles) of 3-amino-2,5-dichlorothiophene hydrochloride in 2.2 l of dimethylformamide at 10° C. in the course of 1 hour, while stirring. The stirring was continued for a further 2 hours at room temperature, after which 1 l of water was added, while stirring. Stirring was continued for a further hour at room temperature, after which the mixture was poured onto 5 l of water, with stirring. The mixture was then filtered under suction, and the residue was washed in succession with 7 l of water, 0.6 l of acetone and 1 l of petroleum ether (boiling range 40°-60° C.) and dried at 50° C. in a drying oven under reduced pressure. 614.5 g (95%) of thiophene-3,4-dicarboxylic acid mono-[N-(2,5-dichlorothien-3-yl)]-amide were obtained in the form of beige crystals of melting point 250°-253° C. (with decomposition).

(b) Thiophene-3,4-dicarboxlyic acid succinimido ester [N-(2,5-dichlorothien-3-yl)]-amide 71.7 g (0.623 mole) of N-hydroxysuccinimide were added to a stirred mixture of 200 g (0.621 mole) of thiophene-3,4-dicarboxylic acid mono-[N-(2,5-dichlorothien-3-yl)]-amide and 3.2 l of tetrahydrofuran. A solution of 128.5 g (0.623 mole) of N,N'-dicyclohexylcarbodiimide was then added dropwise to the stirred mixture in the course of 15 minutes. When the addition was complete, stirring was continued for a further 3 hours, after which the mixture was filtered under suction and the residue was washed with a little tetrahydrofuran. The original filtrate was combined with the tetrahydrofuran used for washing, and then poured onto 6.8 l of petroleum ether (boiling range 40°-60° C.) while stirring. The crystals which were precipitated during this procedure were filtered off under suction, washed with petroleum ether (boiling range 40°-60° C.) and dried at 50° C. in a drying oven under reduced pressure. 251.5 g (97%) of thiophene-3,4-dicarboxylic acid succinimido ester [N-(2,5-dichlorothien-3-yl)]-amide were isolated in the form of beige crystals of melting point 175°-184° C.

(c) 1,3-Dichloro-4,5-dihydrodithieno[3,4-b:3',4'-e]azepine-5,9-dione (III).

109.5 g (116 ml; 1.50 moles) of dimethylformamide were added to 798 g (5.98 moles) of anhydrous aluminum chloride in the course of 15 minutes, while stirring, a highly exothermic reaction taking place. Thereafter, 250 g (0.596 mole) of thiophene-3,4-dicarboxylic acid succinimido ester [N-(2,5-dichlorothien-3-yl)]-amide were added to the stirred mixture at 80° C. in the course of 30 minutes. The reaction mixture was stirred for a further 3 hours at this temperature and then poured, in the warm state and while stirring, onto 4.5 kg of ice and 470 ml (561.2 g; 5.85 moles) of concentrated hydrochloric acid. The crystals precipitated during this procedure were filtered off under suction, washed in succession with 6 l of water, with twice 0.5 l of acetone and with twice 0.5 l of petroleum ether (boiling range 40°-60° C.) and dried at 50° C. in a drying oven under reduced pressure. 170.8 g (94%) of 1,3dichloro-4,5-dihydrodithieno[3,4-b:3',4'-e]azepine-5,9-dione were isolated in the form of beige crystals of melting point 236.5°-239° C.

(d) 4,5-Dihydrodithieno[3,4-b:3',4'-e]azepine-5,9-dione (I)

A mixture of 125 g (0.411 mole) of 1,3-dichloro-4,5-dihydrodithieno[3,4-b:3',4'-e]azepine-5,9-dione, 125 g (1.982 moles) of ammonium formate, 50 g of 5% strength Pd/C, 50 g of active carbon, 3.125 l of propanol and 165 ml of water was refluxed for 3 hours, while stirring, after which 2.5 l of solvent were distilled off under about 100 mbar, while stirring. The residue was poured onto 3 l of ice water, and the resulting suspension was acidified with concentrated hydrochloric acid, while stirring. Stirring was continued for a further hour, after which the mixture was filtered under suction and the residue was added to 1.8 l of dimethylformamide.

The stirred mixture was heated at 100° C. and then filtered again under suction. The residue (Pd/C and active carbon) was washed with 5 times 100 ml of hot dimethylformamide. The original dimethylformamide mother liquor was combined with the dimethylformamide used for washing, and the still warm combined solutions were poured onto 9 l of cold water, while stirring. The precipitate formed during this procedure was filtered off under suction, washed with water and dried at 50° C., in a drying oven under reduced pressure. 80.6 g (83% OF 4,5-dihydrodithieno[3,4-b:3',4'-e]azepine-5,9-dione were obtained in the form of beige crystals of melting point 268.5°–271° C.

EXAMPLE 3

4,5-Dihydrodithieno[3,4-b:3',4'-e]azepine-5,9-dione (I)

A mixture of 5.0 g (0.0164 mole) of 1,3-dichloro-4,5-dihydrodithieno[3,4-b:3',4'-e]azepine-5,9-dione, 4 g of 5% strength Pd/C, 6.3 g (0.034 mole) of tributylamine and 300 ml of propanol was stirred in a hydrogen atmosphere at 80° C. When absorption of hydrogen was complete (after 5 hours), the hot mixture was filtered and the filtrate was poured onto ice water. The resulting suspension was acidified with concentrated hydrochloric acid, and the mixture was then stirred for a short time and filtered under suction. The residue from filtration of the crude reaction mixture was washed several times with hot dimethylformamide. The dimethylformamide used for washing was poured onto ice water, and the precipitate formed was filtered off under suction. The solid thus obtained was combined with the solid product obtained from the propanol filtrate. The total solid product was washed with water and then dried at 50° C. in a drying oven under reduced pressure. 2.9 g (75%) of 4,5-dihydrodithieno[3,4-b:3',4'-e]azepine-5,9-dione were obtained in the form of beige crystals of melting point 268°–271° C.

We claim:

1. A process for the preparation of 4,5-dihydrodithieno[3,4-b:3',4'-e]azepine-5,9-dione, wherein thiophene-3,4-dicarboxylic acid 2,5-dichlorothien-3-ylamide is subjected to a Friedel-Crafts cyclization reaction and the product is then dechlorinated.

2. A process as claimed in claim 1, wherein thiophene-3,4-dicarboxylic acid 2,5-dichlorothien-3-ylamide is activated, prior to the cyclization reaction, by conversion to an ester of the formula IV

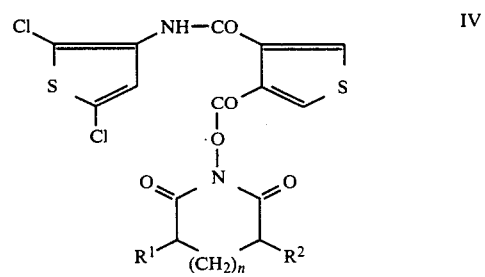

where n is 0, 1 or 2 and $R^1$ and $R^2$ are identical of different and are each $C_1$–$C_4$-alkyl, or, where n is 0, $R^1$ and $R^2$, together with the carbon atoms to which they are bonded, form a benzene nucleus.

3. 1,3-Dichloro-4,5-dihydrodithieno[3,4-b:3',4'-e]azepine-5,9-dione.

4. A compound of the formula IV according to claim 2.

* * * * *